(12) United States Patent
Ely

(10) Patent No.: US 10,052,234 B2
(45) Date of Patent: Aug. 21, 2018

(54) HEARING PROTECTION DEVICE WITH CONVOLUTED ACOUSTIC HORN

(71) Applicant: 3M INNOVATIVE PROPERTIES COMPANY, St. Paul, MN (US)

(72) Inventor: Jacob H. Ely, Indianapolis, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/537,223

(22) PCT Filed: Jan. 14, 2016

(86) PCT No.: PCT/US2016/013439
§ 371 (c)(1),
(2) Date: Jun. 16, 2017

(87) PCT Pub. No.: WO2016/118401
PCT Pub. Date: Jul. 28, 2016

(65) Prior Publication Data
US 2017/0360614 A1 Dec. 21, 2017

Related U.S. Application Data

(60) Provisional application No. 62/104,977, filed on Jan. 19, 2015.

(51) Int. Cl.
*H04R 3/02* (2006.01)
*A61F 11/06* (2006.01)
(Continued)

(52) U.S. Cl.
CPC ............ *A61F 11/08* (2013.01); *H04R 1/1016* (2013.01); *H04R 1/1041* (2013.01);
(Continued)

(58) Field of Classification Search
CPC .. H04R 25/625; H04R 25/65; H04R 2460/11; H04R 1/1008; H04R 1/1016;
(Continued)

(56) References Cited

U.S. PATENT DOCUMENTS 544,732 A 8/1895 Lakin
671,138 A * 4/1901 Knudson et al. .... H04R 25/652
181/130

(Continued)

FOREIGN PATENT DOCUMENTS

CA 1222464 6/1987
CA 2018732 12/1990
(Continued)

OTHER PUBLICATIONS

International Search report for PCT International Application No. PCT/US2016/013439 dated May 31, 2016, 4 pages.
(Continued)

*Primary Examiner* — Xu Mei
(74) *Attorney, Agent, or Firm* — Kenneth B. Wood

(57) ABSTRACT

An earpiece body with a convoluted acoustic horn and a hearing protection device that includes the earpiece body. The convoluted acoustic horn that is configured to receive airborne sound waves through a first, sound-receiving opening and to emit airborne sound waves through a second, sound-emitting opening, wherein the first, sound-receiving opening is larger in cross-sectional area than the second, sound-emitting opening.

23 Claims, 4 Drawing Sheets

(51) Int. Cl.
*A61F 11/08* (2006.01)
*H04R 1/10* (2006.01)
*H04R 25/00* (2006.01)

(52) U.S. Cl.
CPC ...... *H04R 25/652* (2013.01); *A61F 2011/085* (2013.01); *H04R 2460/11* (2013.01)

(58) Field of Classification Search
CPC ..... H04R 1/1041; H04R 1/1083; A61F 11/08; A61F 2011/085
USPC ......... 381/72, 73.1, 328, 380; 181/130, 135; 600/25; 607/57
See application file for complete search history.

(56) References Cited

U.S. PATENT DOCUMENTS

| | | | |
|---|---|---|---|
| 3,930,560 A | 1/1976 | Carlson | |
| 4,143,657 A | 3/1979 | Takeda | |
| 4,349,082 A | 9/1982 | Gastmeier | |
| 4,349,083 A * | 9/1982 | Bennett | H04R 25/48 181/130 |
| 4,407,389 A | 10/1983 | Johnson | |
| 4,418,787 A | 12/1983 | Eggert et al. | |
| 4,527,657 A | 7/1985 | Payne | |
| 4,540,063 A | 9/1985 | Ochi | |
| 4,556,122 A | 12/1985 | Goode | |
| 4,652,414 A | 3/1987 | Schlaegel | |
| 4,852,683 A * | 8/1989 | Killion | A61F 11/10 181/130 |
| 5,113,967 A | 5/1992 | Killion | |
| 5,696,356 A | 12/1997 | Dudley | |
| 5,936,208 A | 8/1999 | Hamery | |
| 6,068,079 A | 5/2000 | Hamery | |
| 6,070,693 A | 6/2000 | Hamery | |
| 6,148,821 A | 11/2000 | Falco | |
| 6,160,895 A | 12/2000 | Dupont | |
| 6,959,093 B2 | 10/2005 | McWilliam | |
| 7,025,061 B2 | 4/2006 | Haussmann | |
| 7,182,087 B1 | 2/2007 | Marsh | |
| 7,708,110 B2 | 5/2010 | Leong et al. | |
| 7,740,104 B1 | 6/2010 | Parkins | |
| 7,743,878 B1 | 6/2010 | Moore | |
| 7,784,583 B1 * | 8/2010 | Hall | H04R 1/1016 181/130 |
| 7,916,884 B2 | 3/2011 | Kah, Jr. | |
| 7,991,179 B2 * | 8/2011 | Drambarean | H04R 1/1016 381/325 |
| 8,340,338 B2 | 12/2012 | Mlodzikowski | |
| 8,428,766 B2 | 4/2013 | Kwon | |
| 8,885,858 B2 | 11/2014 | Nielson | |
| 8,923,543 B2 * | 12/2014 | Sacha | H04R 25/60 181/135 |
| 9,197,959 B2 * | 11/2015 | Fukushima | H04R 1/1058 |
| 9,210,522 B2 * | 12/2015 | Obradovic | H04R 25/652 |
| 9,479,859 B2 | 10/2016 | Henry | |
| 2002/0027996 A1 * | 3/2002 | Leedom | H04R 25/608 381/322 |
| 2006/0042867 A1 * | 3/2006 | Haussmann | A61F 11/08 181/135 |
| 2009/0034775 A1 | 2/2009 | Burton | |
| 2009/0052710 A1 * | 2/2009 | Smith | H04R 25/656 381/328 |
| 2009/0123010 A1 | 5/2009 | Cano | |
| 2009/0136070 A1 | 5/2009 | Koo | |
| 2010/0329475 A1 | 12/2010 | Killion et al. | |
| 2011/0223864 A1 | 9/2011 | Wai | |
| 2011/0255723 A1 | 10/2011 | Obradovic | |
| 2011/0261985 A1 * | 10/2011 | Rung | H04R 25/48 381/328 |
| 2012/0170780 A1 | 7/2012 | Johnson | |
| 2013/0051592 A1 * | 2/2013 | Campbell | H04R 25/656 381/328 |
| 2014/0190494 A1 | 7/2014 | Ely | |
| 2014/0193022 A1 | 7/2014 | Koizumi | |
| 2014/0224568 A1 | 8/2014 | Lederman | |

FOREIGN PATENT DOCUMENTS

| | | |
|---|---|---|
| CN | 202385254 | 8/2012 |
| CN | 203122762 | 8/2013 |
| CN | 203195844 | 9/2013 |
| CN | 104068965 A | 10/2014 |
| DE | 3410388 | 9/1985 |
| EP | 227180 | 7/1987 |
| EP | 13134174 A1 | 5/2003 |
| EP | 1 629 806 A1 | 3/2006 |
| EP | 2436347 | 4/2012 |
| FR | 1.295.320 A | 6/1962 |
| FR | 2676642 | 5/1998 |
| GB | 426246 | 3/1935 |
| GB | 2373667 | 9/2002 |
| JP | 10276498 | 10/1998 |
| JP | 2001/120590 A | 5/2001 |
| JP | 2002/508997 A | 3/2002 |
| JP | 2003-032798 A | 1/2003 |
| JP | 2008-199192 | 8/2008 |
| JP | 2014-007718 A | 1/2014 |
| JP | 3193583 | 9/2014 |
| NL | 9202102 A | 7/1994 |
| WO | WO 99/36016 | 7/1999 |
| WO | WO 02/017836 | 3/2002 |
| WO | WO 2004/002189 A1 | 12/2003 |
| WO | WO 2005-063155 | 7/2005 |
| WO | WO 2009-086649 | 7/2009 |
| WO | WO 2014/094008 A2 | 6/2014 |

OTHER PUBLICATIONS

Examination Report, Application No. 2016209621, dated Sep. 15, 2017, 6 pages.

Search Report, for RU 2017125429, dated Jun. 4, 2018, 3 pages.

* cited by examiner

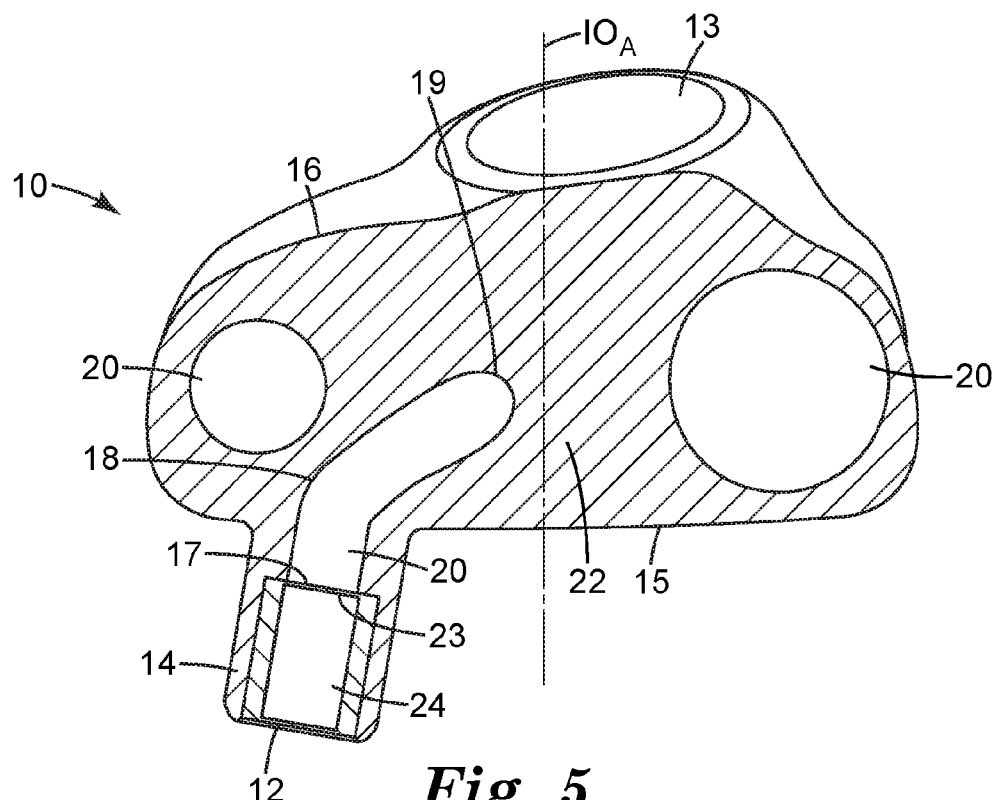
*Fig. 5*
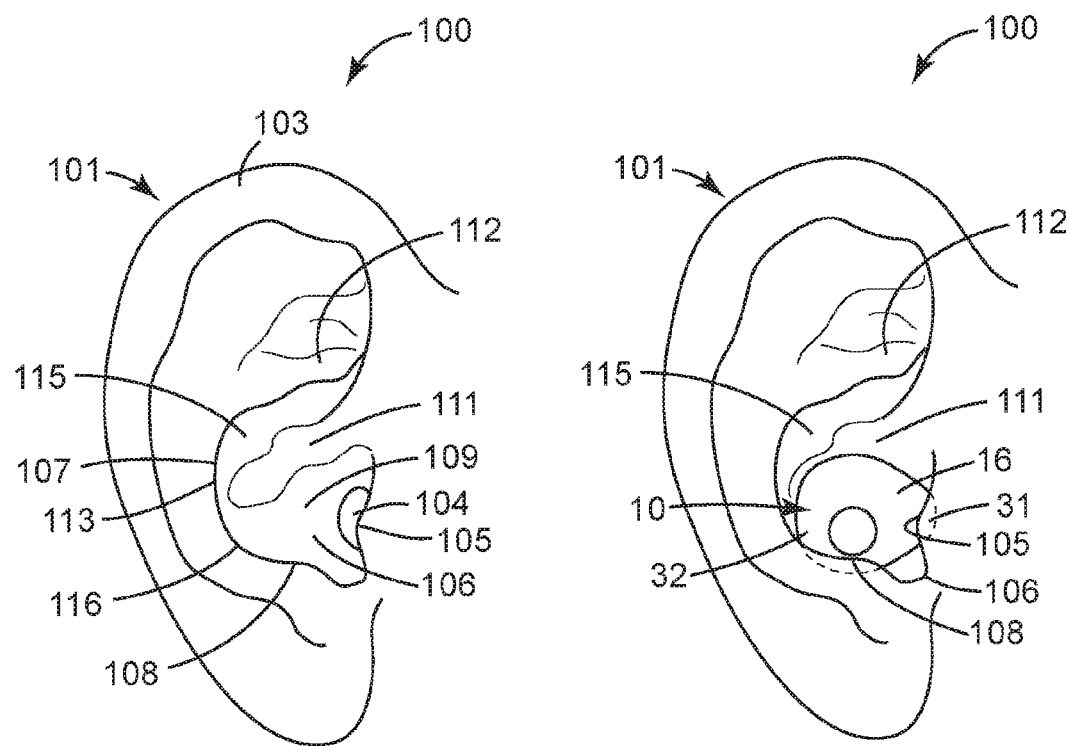
*Fig. 6*  *Fig. 7*

HEARING PROTECTION DEVICE WITH CONVOLUTED ACOUSTIC HORN

BACKGROUND

Hearing protection devices are often used in, for example, industrial, military, and recreational applications.

SUMMARY

In broad summary, herein is disclosed an earpiece body comprising a convoluted acoustic horn; and, a hearing protection device that includes such an earpiece body. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

BRIEF DESCRIPTION OF THE DRAWINGS

FIG. 5 is a cross-sectional view of the exemplary earpiece body of FIG. 3.

FIG. 6 is a side view of a representative human ear.

FIG. 7 is a side view of an exemplary hearing protection device as disclosed herein, as fitted into a human ear.

Figure 1:
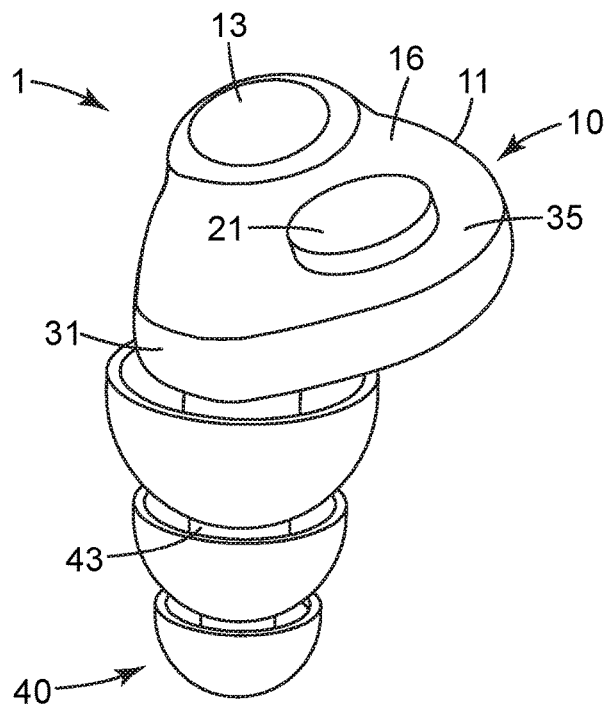
FIG. 1 is a perspective view of an exemplary hearing protection device including an exemplary earpiece body as disclosed herein.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated.

DETAILED DESCRIPTION

For clarity of description of the device disclosed herein and its placement and functioning in a human ear, the following terminology will be adhered to. (Many descriptions presented herein are with respect to a human right ear as viewed in the Figures and to a device fitted therein; it will be understood that corresponding descriptions apply to a human left ear and to a like device fitted therein.) As used herein, "inward" means toward the inner ear of the ear that the device is fitted in; "outward" means away from the inner ear of the ear that the device is fitted in. An inward-outward axis $IO_a$ (as seen e.g. in FIGS. 2, 4 and 5) of an earpiece body means an axis that is oriented at least generally along this direction when the body is fitted into the ear of a user. "Radially inward" and "radially outward" respectively mean radially inward toward, and radially outward away from, this axis (e.g., in a direction at least generally orthogonal to this axis). The terms clockwise and counterclockwise have their customary meaning. Terms such as upper, upward, top, above, and the like; and lower, downward, bottom, below, and the like; have their customary meaning with reference to an axis that runs generally up and down along the human ear (e.g., an earlobe is at the bottom of the human ear).

As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties). The term "substantially", unless otherwise specifically defined, means to a high degree of approximation (e.g., within +/−10% for quantifiable properties). The term "essentially" means to a very high degree of approximation (e.g., within plus or minus 2% for quantifiable properties); it will be understood that the phrase "at least essentially" subsumes the specific case of an "exact" match. However, even an "exact" match, or any other characterization using terms such as e.g. same, equal, identical, uniform, constant, and the like, will be understood to be within the usual tolerances or measuring error applicable to the particular circumstance rather than requiring absolute precision or a perfect match. All references herein to numerical parameters (dimensions, ratios, and so on) are understood to be calculable (unless otherwise noted) by the use of average values derived from a number of measurements of the parameter, particularly for the case of a parameter that is variable.

Figure 2:
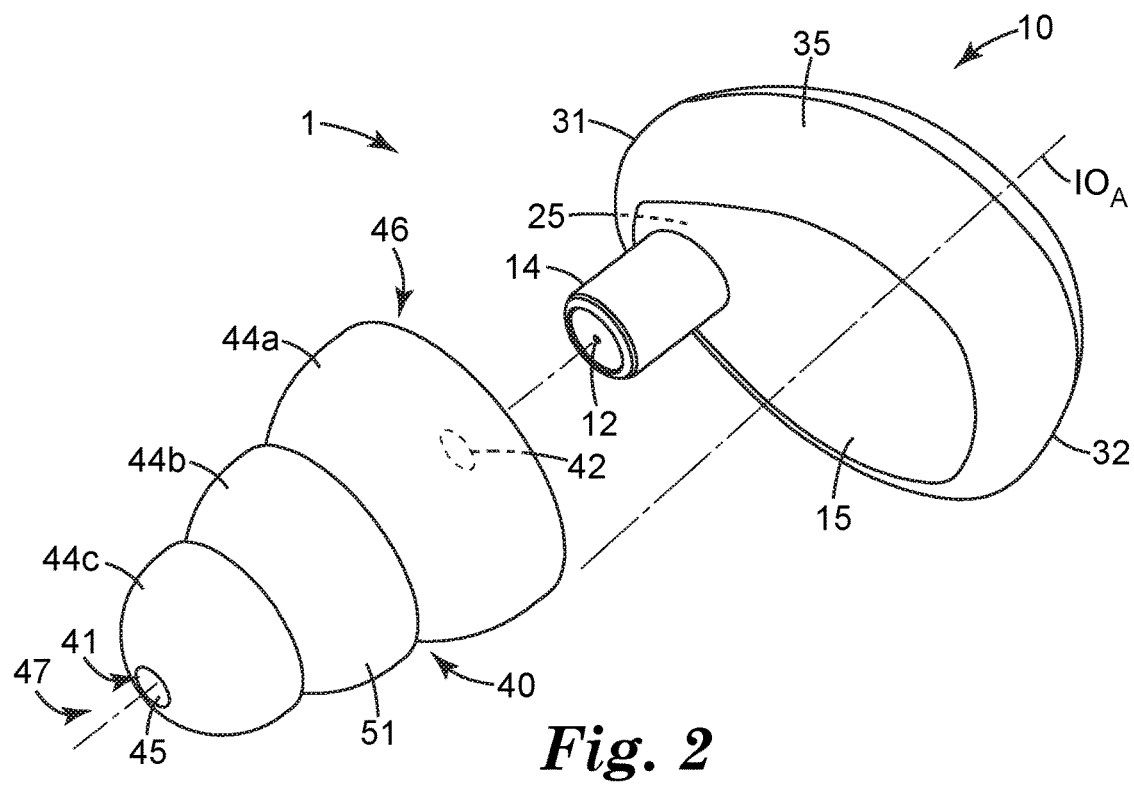
FIG. 2 is a alternative perspective, exploded view of the device of FIG. 1.

As shown in exemplary embodiment in FIG. 1, disclosed herein is a hearing protection device 1 that is suitable for fitting into the concha of a human ear. In at least some embodiments, device 1 is a passive device, which will be distinguished from an electronic hearing protection device. As shown in FIGS. 1 and 2, device 1 is comprised of two major components—eartip 40 and earpiece body 10. Earpiece body 10 is configured (i.e., shaped and sized) to reside in the concha of a human user's ear and is configured to receive airborne sound which passes into, and through, a convoluted acoustic horn 20 (most easily seen in FIGS. 3 and 4), and is then emitted therefrom to be received by eartip 40. Eartip 40 is configured (i.e., is shaped and sized and is comprised of a material of suitable softness) to fit into the ear canal of the user's ear (this terminology broadly denotes that at least a portion of eartip 40 fits into an outward portion of the ear canal and does not imply that the entirety of eartip 40 must be fitted into the ear canal). In at least some embodiments eartip 40 is detachably attached to earpiece body 10 so that eartip 40 can be removed and cleaned or replaced if desired. In other embodiments eartip 40 may be supplied along with earpiece body 10, e.g. non-detachably attached thereto.

Figure 3:
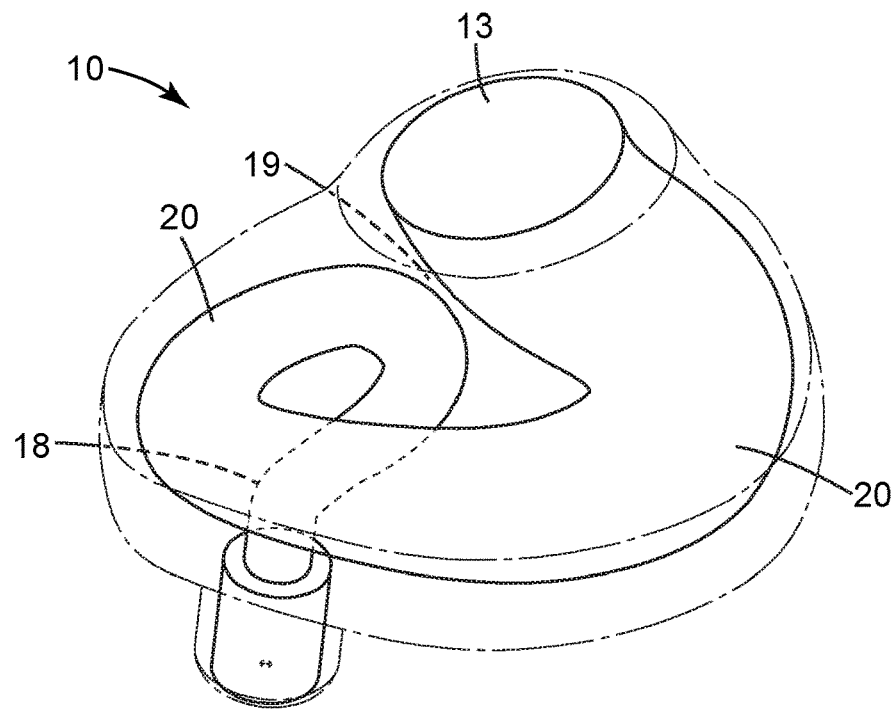
FIG. 3 is a perspective view of an exemplary earpiece body, with the body shown in partial transparency to reveal an exemplary convoluted acoustic horn.
Figure 4:
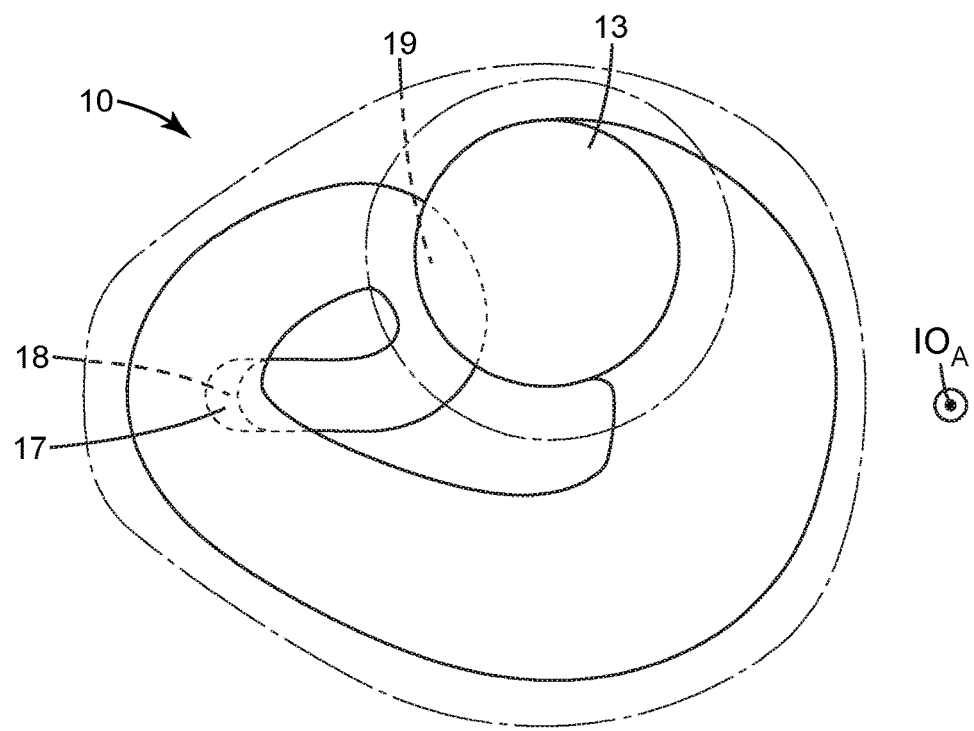
FIG. 4 is a view of the exemplary earpiece body of FIG. 3, viewed along an inward-outward axis of the earpiece body and shown in partial transparency.

An exemplary earpiece body 10 is shown in FIGS. 1 and 2 (in combination with an eartip 40) and in isolated view in FIGS. 3-5. Earpiece body 10 comprises a housing 11 which may be comprised of e.g. a molded polymeric material. In some embodiments, housing 11 may be formed by mating together two major housing parts, e.g. inward and outward major housing parts. In other embodiments, housing 11 (and e.g. the entirety of earpiece body 10) may be comprised of a single entity, made e.g. by 3D printing. Housing 11 at least partially defines an interior 22 (seen e.g. in FIG. 5), within which is provided convoluted acoustic horn 20, described in detail later herein. It is emphasized that the cross-sectional view of FIG. 5 is merely an idealized representation in which most portions of earpiece body interior 22 other than acoustic horn 20 are depicted as solid. This is done for ease of visualizing acoustic horn 20; in many embodiments interior 22 of earpiece body 10 may comprise one or more void spaces in addition to the void spaces that collectively provide acoustic horn 20. Such additional void spaces may e.g. provide room for other components or features as discussed later herein.

In at least some embodiments, housing 11 may be comprised of a rigid or semi-rigid material, e.g., a material that is not as soft and deformable as the material of eartip 40. In various embodiments, housing 11 may be comprised of an organic polymeric material (e.g., a thermoplastic injection-molding resin) with a hardness of at least about 70, 80, 90 or 100 on a Shore A scale.

Acoustic Horn

Earpiece body 10 comprises an acoustic horn 20, as seen in exemplary embodiment in FIGS. 3-5. By definition an acoustic horn comprises a first, sound-receiving opening 13 (i.e., an entrance) and a second, sound-emitting opening 17 (i.e., an exit, as seen e.g. in FIG. 5) that are fluidly connected with each other so that airborne sound that enters the entrance can travel through the horn to be emitted from the exit. By definition, sound-receiving entrance 13 is larger in area than sound-emitting exit 17, so that entrance 13 functions as a "mouth" of the horn while exit 17 functions as a "throat" of the horn.

In some embodiments, sound-receiving entrance 13 is an at least generally outward-facing opening (as evident e.g. in FIGS. 1 and 3, and particularly in FIG. 5), meaning that it faces at least generally outward along the inward-outward axis $IO_a$ of earpiece body 10. In other embodiments, sound-receiving entrance 13 may be an at least generally inward-facing opening. In at least some embodiments, sound-emitting exit 17 is an at least generally inward-facing opening (noting that in the exemplary embodiment of FIG. 5, exit 17 is generally inward-facing albeit at a slight angle away from the inward-outward axis $IO_a$).

Acoustic horn 20 is a convoluted horn with the term convoluted having its ordinary meaning; i.e., horn 20 follows a path (along the length of the horn from entrance 13 to exit 17) that is at least e.g. generally tortuous, serpentine, coiled or spiral. Such a convoluted horn (as seen most easily in the exemplary embodiment of FIGS. 3 and 4) is distinguished from e.g. a "hairpin" horn that, along its length, comprises only a single, sharply-bending portion with the remainder of the horn length being relatively straight.

In some embodiments, acoustic horn 20 may be a helical horn, meaning that at least a significant portion (meaning at least about 35 percent) of the length of horn 20 exhibits a helical path that moves in an inward direction in traversing the length of the horn from entrance 13 to exit 17. Such a helical horn path is distinguished from an at least substantially flat-spiral path in which most or essentially all of the path is in a plane that is at a relatively constant location along the $IO_a$ axis. In further embodiments in which acoustic horn 20 is a helical horn, at least 40, 50, 60, 70, or 80 percent of the path length of the horn exhibits a helical path.

For the purpose of measuring a path length (or any other characterization of horn 20), the "path" of horn 20 is traced along the centerline of horn 20 from entrance 13 to exit 17. (As discussed later in detail and as evident e.g. in FIG. 5, exit 17 of horn 20 does not necessarily have to be the same opening as the sound-emitting opening (12 in FIG. 5) through which airborne sound leaves earpiece body 10.) For the simple case of a horn in which the cross-sectional area of the horn is circular along the length of the horn, such a path would simply be a centerline trace that followed the horn from entrance to exit, connecting the geometric centers of each successive circular cross-section down the length of the horn. For other shapes (e.g., squares, rectangles, isosceles triangles and the like) such a path would similarly follow the geometric center of each successive cross-section along the length of the horn. For e.g. irregular shapes, non-isosceles triangles, and so on, the centroid (barycenter) of each successive cross-sectional slice of the horn can be used to establish the path. If a horn varies in cross-sectional shape along its length, any of these may be used in combination as needed.

In some embodiments, acoustic horn 20 may exhibit at least one underpass feature. An underpass feature is one in which, when the horn is viewed from the outward side looking inward along the inward-outward axis $IO_a$ as in FIG. 4), at least a portion of a cross-sectional area of an inward portion of the horn inwardly underlies at least a portion of a cross-sectional area of an outward portion of the horn (and is separated therefrom by some volume of interior 22 of earpiece body 10 that is not part of the acoustic horn). That is, when viewed in this manner, such an inward portion of the horn at least partially passes inwardly under the outward portion of the horn. Two such underpass features 18 and 19 are visible in FIGS. 3 and 5, and particularly in FIG. 4. In various embodiments, acoustic horn 20 may have none, one, two, three, four, or more underpass features.

Offset Opening(s)

In some embodiments, second, sound-emitting opening (exit) 17 of convoluted horn 20 may be an offset opening. By this is mean that when viewed along inward-outward axis $IO_a$ of the earpiece body, opening (exit) 17 of horn 20 does not overlap the geometric center (centroid) of earpiece body 10. The view (along the inward-outward axis) of FIG. 4 thus reveals that exemplary exit 17 as shown therein is an offset opening. It will be appreciated that a horn exit that is offset in this manner (as opposed to e.g. a horn exit located substantially in the geometric center of an earpiece body) may advantageously allow a larger earpiece body (and thus a larger and/or longer horn) to be used without some portion of the earpiece body impinging on some portion (e.g. the tragus and/or antitragus) of the user's ear, which might cause discomfort.

In some embodiments, first, sound-emitting opening (entrance) 13 of convoluted horn 20 may be an offset opening. By this is mean that when viewed along inward-outward axis $IO_a$ of the earpiece body, opening (entrance) 13 of horn 20 does not overlap the geometric center (centroid) of earpiece body 10. In some embodiments, entrance 13 and exit 17 are arranged so that horn 20 takes the form of an offset spiral. By this is meant that (again when viewed along the inward-outward axis) no portion of exit 17 overlaps with any portion of entrance 13. The view of FIG. 4 thus reveals that exemplary horn 20 as shown therein is in the form of an offset spiral.

In some embodiments, acoustic horn 20 may take the form of an eccentric spiral when viewed along an inward-outward axis of the earpiece body. By eccentric is meant that the spacing between concentrically neighboring segments (as measured between the above-discussed centerlines of the segments) of the horn is not constant. The exemplary horn of FIG. 4 is thus seen to take the form of an eccentric, and offset, spiral. It will be appreciated that such arrangements may e.g. advantageously allow room in interior 22 of earpiece body 10 for internal components, mechanisms and the like (for example, components associated with a valve 25 as discussed later herein). In some embodiments, horn 20, when viewed along an inward-outward axis of the earpiece body, may (as ascertained by following the above-described centerline path of the horn) make at least 0.5, 0.8, 1.0. 1.2, or 1.4 revolutions along the length between entrance 13 and exit 17. In further embodiments, horn 20 may make less than 2.0, 1.8, or 1.6 revolutions along this length (the exemplary horn of FIG. 4 appears to make approximately 1.5 revolutions).

The ordinary artisan will appreciate that acoustic horn 20 may advantageously allow airborne sound of at least certain frequencies to be received (gathered) by entrance 13 and transmitted down the length of horn 20 to leave horn 20 through exit 17. The decreasing cross-sectional area of horn 20 will provide that the sound waves increase in intensity during the journey down horn 20. The providing of an acoustic horn 20 in an earpiece body can thus, for at least certain frequencies, at least partially offset the insertion loss that often occurs when an earpiece body is inserted into the concha thus disrupting the natural sound-gathering effect of the external ear.

The horn effect is thus achieved by providing that horn entrance 13 is larger than horn exit 17. In various embodiments, the area of the first, sound-receiving opening (entrance) 13 may be greater than the area of the second, sound-emitting opening by an incremental percentage of from about 150 to about 1400. In further embodiments, the area of the entrance may be greater than that of the exit by an incremental percentage of about 200 to about 1000, or about 250 to about 600. The incremental percentage is calculated using the smaller, exit opening as a basis. For example, given an opening with an area of 37.0 mm$^2$ and an exit with an area of 2.7 mm$^2$, the opening would be greater in area than the exit by an incremental percentage of (37.0–2.7)/2.7 or about 1270. (Strictly speaking, the area of entrance 13 as used in such calculations will be the effective area, exclusive of any area obstructed by solid materials of e.g. a mesh or screen that is not acoustically transparent at the sound frequencies of interest, as discussed later in detail).

In various embodiments, the area of horn entrance 13 may be at least about 25, 30, or 35 mm$^2$. In further embodiments, the area of horn entrance 13 may be at most about 50, 45, or 40 mm$^2$. In various embodiments, the area of horn exit 17 may be at least about 1.5, 2.0, or 2.5 mm$^2$. In further embodiments, the area of horn exit 17 may be at most about 4.0, 3.5, or 3.0 mm$^2$. In various embodiments, the length of horn 20 from entrance 13 to exit 17 may be at least about 3.0, 3.5, 3.8, or 4.0 cm. In further embodiments, the length of horn 20 may be at most about 5.5, 5.0, 4.5, 4.2, or 4.0 cm.

The fact that exit 17 is smaller in area than entrance 13 will result in horn 20 exhibiting a taper. In various embodiments, horn 20 may exhibit an overall taper (measured over the entire horn length) that is at least about 50, 100, 150, 200, 250, 300, or 350 incremental percentage per centimeter of horn length. In further embodiments, horn 20 may exhibit an overall taper that is at most about 450, 400, 350, or 300 incremental percentage per centimeter of horn length. By way of specific example, a horn with an entrance of 37.0 mm$^2$ in area and an exit area of 2.7 mm$^2$ in area, and with a length of 4 cm, would exhibit an incremental taper of ([37.0–2.7]/2.7)/4, or about 320 incremental percentage per cm of horn length. The local taper at any particular point along the length of horn 20 may vary from the overall taper, or course. That is, in some cases the taper may be more pronounced at some locations, and less pronounced at other locations. One exemplary version of this would be a design in which horn 20 exhibits a few (e.g., four, three, two, or even one) step changes in area over the length of horn 20. While such designs are within the scope of an acoustic horn as disclosed herein, in other embodiments horn 20 may exhibit an at least substantially constant taper, meaning that the local taper is within plus or minus 10% of the overall average taper, over at least a substantial portion (i.e., 80%) of the path length. In this context, a constant taper does not include the particular case of a zero or near-zero (i.e., less than 10 incremental percentage per cm of horn length) taper. In particular embodiments, horn 20 is smoothly-tapered, meaning that as the length of horn 20 is traversed from entrance 13 to exit 17, the area of the horn does not increase at any point along the length of the horn. While it may be convenient that horn 20 have an at least generally circular shape at any or all locations along the length of horn 20, the shape is not particularly limited and, at any given location along its length, horn 20 may have any suitable shape (e.g., square, rectangular, oval, triangular, irregular, and so on). In various embodiments, horn 20 may have a shape corresponding at least generally, substantially, or essentially, to a conical horn, an exponential horn, or a tractrix horn.

In at least some embodiments, entrance 13 and exit 17 are the only openings (by which airborne sound waves can enter or exit horn 20) in horn 20. Horn exit 17 by definition is the inward end of horn 20. As noted elsewhere herein, horn exit 17 may not necessarily correspond to an inwardmost and/or terminal opening of earpiece body 10 (for example, in the exemplary design shown in FIG. 5, horn exit 17 is distinguished from sound-emitting outlet 12 of earpiece body 10, outlet 12 being located at an inwardmost location of earpiece body 10).

In some embodiments, horn entrance 13 may be a substantially unobstructed opening, meaning that no more than 20% of the potentially available area of the opening is obstructed by an air-impermeable material (e.g., by solid portions of a screen, mesh, perforated plate, or the like, or by some other item). In further embodiments, horn entrance 13 is an unobstructed opening, meaning that no portion of the potentially available area of the opening is obstructed by an air-impermeable material. In the exemplary embodiment shown in FIGS. 1 and 4, entrance 13 is an unobstructed opening, since no portion of the total potentially available area (i.e., the area bounded by the circular rim that defines opening 13) is obstructed. Such embodiments can be contrasted with e.g. designs in which a significant portion, or even a majority, of the potentially available area of an opening is obstructed. A particular example of an obstructed opening would be an opening in which a cylindrical member is positioned within much of the opening so that the usable area of the opening that is available for collecting sound waves, is an annulus that has a much lower area than would have been available had the entire area of the opening been used.

It will be appreciated that a convoluted horn design as disclosed herein can allow a relatively long horn length to be achieved even with an earpiece body that is relatively unobtrusive in size and appearance and in particular is relatively low-profile (e.g., does not protrude significantly out of the concha). This relatively long horn length, in combination with a taper as disclosed herein, can provide that acoustic horn 20 exhibits a cutoff frequency (below which little or no sound may be effectively gathered and/or intensified) in the range of about 2 KHz. This can provide that acoustic horn 20 can selectively amplify sound in wavelength ranges that are most useful e.g. for human speech intelligibility; that is, sound in the range of e.g. 2 KHz and above. (Strictly speaking, horn 20 may not be considered as "amplifying" such sound over what would be heard in the absence of earpiece body 10 being present in the user's ear; rather, horn 20 is helping to compensate for the insertion loss that occurs upon the placement of earpiece body in the ear thus disrupting the external ear's natural sound-gathering and collecting ability).

In particular embodiments, using a level-dependent sound-attenuating feature (e.g., a level-dependent acoustic filter as discussed later herein) in combination with horn 20 in a hearing protection device 1, can provide that device 1 can allow enhanced human speech intelligibility, while still allowing device 1 to adequately protect the user from loud sounds. Also as noted later herein, in further embodiments, providing a valve at some location along the complete acoustic pathway through device 1 can, if desired, allow device 1 to be reversibly converted into a "closed" earplug (e.g. if the user is in an environment in which relatively high-intensity sound is frequently or constantly present and thus in which the highest possible sound-blocking is desired).

Earpiece body 10 comprises an at least generally inward-facing, airborne-sound-emitting outlet 12 (most easily seen in FIGS. 2 and 5) that may be conveniently provided in a location which allows a primary, sound-receiving opening 42 of through-passage 41 of eartip 40 to be acoustically mated thereto. By "acoustically mated" is meant that outlet 12 of earpiece body 10 and the primary, sound-receiving opening 42 of eartip 40 are fluidly connected with each other so that sound waves emitted from outlet 12 are able to travel (e.g., directly) therefrom into opening 42. In an exemplary embodiment most easily seen in FIGS. 2 and 5, outlet 12 may be provided proximate the terminal end of a hollow protrusion 14 (e.g., post) that extends inward (when device 1 is fitted into a user's ear), so that when outward end 46 of eartip 40 is attached to protrusion 14, outlet 12 of earpiece body 10 and opening 42 of eartip 40 are aligned with each other and in close proximity to each other. (In many embodiments outward end 46 of eartip 40 may be pushed onto protrusion 14 e.g. to provide a secure connection via a compression fit, so that strictly speaking, the opening 42 of eartip 40 that receives the sound emitted from outlet 12, may be located somewhat inward along through-passage 41 of eartip 40 rather than being at the outward terminus of through-passage 41). In some embodiments, protrusion 14 of earpiece body 10 may be of the same composition and properties (e.g., made of the same material) as housing 11 of earpiece body 10. In particular embodiments, protrusion 14 may be an integral portion of housing 11 (which condition encompasses the case that protrusion 14 is an integral portion of a major housing part, in the specific instance that housing 11 is formed by the mating together of two major housing parts).

In some embodiments, eartip 40 may be attached to earpiece body 10 (e.g., outward end 46 of eartip is attached to protrusion 14 of earpiece body 10) in a detachable manner. By this is meant that a user can manually (i.e., with fingers alone, without the use of any special tools such as pliers, screwdrivers, pry bars, and so on) separate eartip 40 from earpiece body 10 so as to e.g. clean eartip 40, replace it with a new or cleaned eartip, and so on. In the particular embodiment shown in FIGS. 1 and 2, detachable attachment of eartip 40 to earpiece body 10 may be provided by a friction fit of an annular portion of main body 43 of eartip onto the radially outer surface of protrusion (post) 14. (Here and elsewhere, the term annular is used broadly and does not imply or require a strictly or even substantially circular geometry). It will be appreciated however that any suitable method of detachably attaching eartip 40 to earpiece body 10 can be used.

In at least some embodiments, device 1 may include at least one level-dependent sound-attenuating physical (i.e., non-electronic) feature 23. Such a feature will, at least at some frequencies, attenuate high-intensity sound more than it will attenuate low-intensity sound. Such a feature may take the form of e.g. one or more orifices, restrictions, or obstructions at some location along the length of a sound-transmissive elongate passage, which feature provides a significantly reduced cross-sectional area for passage of sound therethrough, when compared to the average diameter of the passage 41. Such a level-dependent sound-attenuating feature may be located in any suitable sound-transmissive passage, e.g. at any point along the length of acoustic horn 20, or at any point along the length of through-passage 41 of eartip 40. However, in particular embodiments, it may be advantageous to locate such a feature 23 between the second, sound-emitting opening (exit) 17 of acoustic horn 20 and the primary, sound-receiving opening 42 of the eartip 40 so that any airborne sound that is emitted from exit 17 of the acoustic horn must encounter the sound-level-dependent sound attenuating physical feature before reaching the primary, sound-receiving opening 42 of the eartip. Such an arrangement is shown in exemplary embodiment in FIG. 5. In the exemplary design of FIG. 5, the sound-level-dependent sound attenuating physical feature is a level-dependent acoustic filter 23 that is fitted into a chamber 24 defined at least partially by surfaces molded into the interior of protruding post 14 of earpiece body 10. In configurations of this general type, airborne sound that is emitted from the second, sound-emitting opening 17 of acoustic horn 20 must pass through acoustic filter 23 in order to exit earpiece body 10 (via outlet 12) to reach primary, sound-receiving opening 42 of eartip 40.

Any suitable level-dependent acoustic filter may be used. Various potentially suitable acoustic filters are described in detail e.g. in U.S. Pat. Nos. 6,148,821, 6,070,693, 6,068,079, and 5,936,208, and in US Patent Application Publication No. 2014/0190494. In the specific embodiment depicted in FIG. 5, acoustic filter 23 is a hollow, generally drum-shaped entity with a relatively small-diameter aperture at at least one end thereof, that is fitted (e.g. compression-fitted, and/or held by adhesive or any other means) into chamber 24.

In specific embodiments, a level-dependent sound-attenuating physical feature (e.g., an acoustic filter) located at the above-described position is the only such feature that is present in device 1. That is, in some embodiments no level-dependent sound attenuating physical feature or features are present in passage 41 of eartip 40. For example, in some embodiments passage 41 might be e.g. a hollow conduit with an average diameter (or equivalent diameter) that does not vary by more than e.g. plus or minus 20% along its length. Similarly, in some embodiments no such level-dependent sound attenuating physical feature or features are located anywhere along the length of acoustic horn 20.

The ordinary artisan will understand that in the exemplary design shown in FIG. 5, the above-described exit 17 represents the inward end of acoustic horn 20; chamber 24 and acoustic filter 23 therein are not part of acoustic horn 20 (nor is passage 41 of eartip 40). The ordinary artisan will further understand that such an arrangement is distinguished from designs in which an acoustic filter/damper is apparently placed at some location within the length of an acoustic horn (e.g., between halfway and two-thirds along the length of the horn). The ordinary artisan will appreciate that locating an acoustic filter/damper within the length of an acoustic horn may disadvantageously affect the functioning of the horn (and in fact might effectively divide the horn into two separate horns in series, with disadvantageous results). The ordinary artisan will thus understand that locating any such level-dependent sound-attenuating physical feature (e.g. an acoustic filter) as disclosed herein may advantageously allow acoustic horn 20 to be used to maximum effectiveness.

If desired, earpiece body 10 may comprise at least one valve 25 that may be actuated to partially or completely close acoustic horn 20 so that no airborne sound may be transmitted therethrough. Such a valve may be of any suitable type (e.g. a gate valve comprising a member that can open or close by sliding, bending, and/or partially rotating about a pivot (e.g. hinge). Such a valve may be located at any position along the length of acoustic horn 20. In some embodiments, such a valve may be located proximate the second, sound-emitting opening (exit) 17 of acoustic horn 20 (as in the exemplary depiction of FIG. 2).

Valve 25 may be actuated e.g. by a mechanical switch 21 of any suitable type (e.g., a rocker switch, a sliding switch, a rotatable switch, a button switch, and so on). Such a mechanical switch may be in any suitable location of housing 11 of earpiece body 10. In some embodiments, switch 21 may be conveniently located on outward surface 16 of earpiece body 10, so that it may be operated without necessarily having to remove device 1 from the ear. In particular embodiments, valve 25 may be located proximate second, sound-emitting opening 17 of acoustic horn 20, while switch 21 is located on outward surface 16 of earpiece body 10 (that is, in a location that is remote from valve 25). In such embodiments, switch 21 and valve 25 may be operatively coupled to each other e.g. by way of one or more pushrods, cables, or the like, in order to facilitate operation of valve 25 by switch 21. It will be appreciated that the convoluted design of acoustic horn 20, e.g. in combination with the providing of additional void spaces within interior 22 of earpiece body 10, may advantageously facilitate such arrangements.

In general, housing 11 of earpiece body 10 can be configured so as to minimize (e.g., at least substantially prevent) the entry of ambient airborne sound into interior 22 of earpiece body 10 except through the desired pathway provided by acoustic horn 20. This may be done by e.g. minimizing the number and size of any through-openings in housing 11. Thus in some embodiments, earpiece body 10 does not have any (unoccluded) openings that lead into interior 22 of earpiece body 10 other than the first, sound-receiving opening 13 of acoustic horn 20, and the sound-emitting outlet 12 of earpiece body 10.

In further detail, at any location of housing 11 at which a through-opening might be necessary to accommodate a component such as e.g. a switch, such a component may be mated to its through-opening so that it at least substantially occludes the opening (e.g., to form a tight seal). To aid in this, any suitable gasket, sealant, adhesive, or the like, can be used in mounting any such component to a through-opening in housing 11. (Similarly, if two or more housing pieces are mated together to form housing 11, any suitable gasket, sealant, adhesive, or the like may used to similar effect.) Beyond this, in at least some embodiments acoustic horn 20 may be configured so that it comprises no openings other than the aforementioned entrance 13 and exit 17. So, any stray airborne noise that may penetrate into interior 22 of earpiece body 10, may be at least substantially prevented from entering horn 20. Likewise, any stray airborne noise that may penetrate around the outside of earpiece body 10 may be at least substantially prevented (by way of the above-described external occluding achieved by eartip 40) from flowing around the outside of eartip 40 to reach the inner ear of the user. Still further, a tight seal between eartip 40 and e.g. protrusion 14 of earpiece body 10 may at least substantially prevent any stray airborne noise that may penetrate around the outside of earpiece body 10, from penetrating into internal passage 41 of eartip 40. Such arrangements, however achieved, can provide that e.g. at least substantially all the airborne sound that reaches the inner ear of a user, is sound that has entered acoustic horn 20 through entrance 13 thereof and has passed through acoustic horn 20, with advantageous results as discussed herein.

If desired, any suitable protective element may be positioned outward of at least a portion of horn entrance 13 e.g. to minimize the entry of debris into horn 20. Such a protective element may be e.g. a mesh, screen, perforated plate, etc., and may be made of any suitable material. It may be removable and cleanable and/or replaceable if desired. If the solid materials of the protective element are e.g. sized and arranged so that the element is at least substantially acoustically transparent, the element may be ignored e.g. for purposes of calculating the area of opening 13 (i.e., the overall or nominal area may be used). However, if the solid materials of the protective element do have a non-negligible effect on airborne sound transmission, the "effective" area of opening 13, modified e.g. in view of the % open area of any protective element that blocks a portion of the opening, may be used in such calculations.

An exemplary eartip 40 is shown in FIG. 1 and in isolated view in FIG. 2. Eartip 40 comprises a through-passage 41, that extends through eartip 40 from outward end 46 to inward end 47 and allows the passage of airborne sound therethrough. In at least some embodiments, through-passage 41 is an internal through-passage, meaning that throughout all of its length, passage 41 is radially surrounded by material of eartip 40 (rather than being e.g. a groove or channel that is open to a radially outermost surface of eartip 40). Through-passage 41 (which may be at least generally aligned with a long axis of eartip 40, e.g. as depicted in FIG. 2) comprises a primary sound-receiving opening (e.g., opening 42 as depicted in FIG. 2) that, when eartip 40 is attached to earpiece body 10, receives airborne sound from earpiece body 10. Through-passage 41 further comprises a secondary, sound emitting opening 45 that faces toward the inner ear of the user, so that airborne sound can be transmitted through internal through-passage 41 and directed therefrom toward the inner ear of the user.

In at least some embodiments, the fitting of at least a portion of eartip 40 into at least a portion of the ear canal externally occludes the ear canal. By externally occludes is meant that at least some radially outward surfaces (e.g., surfaces 51) of the eartip are in sufficient contact with portions of the walls of the ear canal to substantially prevent ambient airborne sound from traveling along the ear canal in a space otherwise existing between the eartip and the ear canal walls so as to reach the inner ear. This can provide that at least substantially all, or essentially all, of the airborne sound that reaches the inner ear, does so by way of internal through-passage 41 (and thus has passed through the acoustic horn of the earpiece body, as discussed above). Eartip 40 may be tightly fitted to earpiece body 10 (e.g., in an at least substantially leak-proof manner) to further provide that any airborne sound that reaches the inner ear has passed through the acoustic horn of the earpiece body, again as noted above.

In further detail, by eartip is meant a body of which at least major portions thereof are resiliently compressible and/or deformable at least in a radially inward direction, so that when the eartip is inserted into an ear canal, at least some portions of the eartip are resiliently biased radially outward so that at least some radially outward surfaces of the eartip are held against portions of the walls of the ear canal so as to substantially or completely eliminate any air gap therebetween. Eartip 40 comprises a long axis L that, when device 1 is fitted in the ear of a human user, will typically be at least generally aligned with a long axis of the portion of the ear canal into which the eartip is fitted. Eartip 40 comprises an outward end 46 and an inward end 47, end 46 being the end that is attached (whether permanently or detachably) to earpiece body 10 and end 47 being the end that resides closest to the inner ear of the user. Eartip 40 may be comprised of any suitable material or materials, in any suitable geometric configuration. In some embodiments, eartip 40 may be comprised of a resiliently deformable and/or compressible organic polymeric material, e.g. a suitable molded plastic material. In embodiments of a first general type, the desired resilient compressibility of the eartip may be provided by properties of the organic polymeric material alone rather than by e.g. any particular geometric design. For example, in some embodiments eartip 40 might consist of a generally cylindrical and/or tapered main body, comprised e.g. of a resiliently compressible foam. In embodiments of a second general type, the desired resilient compressibility may be provided or enhanced by the geometric design of at least some components of the eartip. For example, as shown in exemplary manner in FIGS. 1 and 2, an eartip 40 may comprise a main body (e.g., trunk) 43 comprising one or more radially-outward-protruding flanges 44 made of a resiliently deformable material. Insertion of such an eartip into an ear canal may result in such flanges being deformed (e.g., swept back toward outward end 46 of the eartip), with the desired resilient biasing of surfaces of the flanges against the walls of the ear canal being thus achieved. In specific embodiments, one or more flanges 44 may be provided already in a swept-back (flared or bell-like) configuration even before being inserted into an ear canal (as shown in exemplary manner in FIGS. 1 and 2). In particular embodiments, such flanges may be at least generally semi-hemispherical in shape. It will be appreciated that in embodiments of this second general type, it may not be necessary that all, or even any, of the material of which eartip 40 is made must be significantly compressible, as long as at least certain components (e.g., flanges) of the eartip are resiliently deformable and are provided in geometric shapes that allow such deformation to provide the desired resilient biasing of surfaces of such components against the ear canal walls.

In some embodiments (whether eartip 40 comprises flanges or not), eartip 40 (e.g. main body 43 and any flanges that may be present) may consist of a single (e.g., molded) piece of organic polymeric material, e.g. a resiliently deformable and/or compressible material. In other embodiments, eartip 40 might comprise e.g. a main body that is not necessarily resilient and/or compressible, but radially outwards of which main body is mounted one or more resiliently deformable flanges, one or more annular layers of a resiliently compressible material, or the like. (It will be appreciated that in designs of the general type shown in FIGS. 1-3, it may be desirable that at least the outward portion of main body 43 of eartip 40 may be resiliently deformable, in order to facilitate e.g. the stretch-fitting of an outward opening (e.g., 42) of eartip 40 over protrusion 14 of earpiece body 10).

In some embodiments, eartip 40 may exhibit a tapered shape with inward end 47 (that faces toward the inner ear) being the narrow end, whether eartip 40 is in the form of a single piece, or whether such a tapered shape is provided stepwise by a plurality of flanges of different diameters. Although three flanges (44a, 44b, and 44c) each with ear canal wall-contacting surfaces are shown in FIGS. 1 and 2, any number of flanges might be used. It will be appreciated that a wide variety of arrangements are possible and that the particular designs depicted in FIGS. 1 and 2 are merely exemplary embodiments. In various embodiments, a resiliently deformable and/or compressible portion of eartip 40 (or the entirety thereof), may be made of a material that exhibits a hardness of less than about 50, 45, 40, 35, 30, 25, or 20 on a Shore A scale. In particular embodiments, such an eartip or a portion thereof may be made of a material that exhibits a hardness of from about 30 to about 40 on a Shore A scale. Whatever the specific design of eartip 40, at least some portion of eartip 40 may conveniently be chosen to have a radial diameter that (when the components of eartip 40 are in an undeformed and/or uncompressed state) is at least somewhat larger than the average diameter of the outer ear canal of an adult human, in order to provide that insertion of eartip 40 into the ear canal will achieve the desired resilient biasing of surfaces of the eartip against the walls of the ear canal. While an exemplary style of eartip has been described in detail, it is emphasized that the herein-described earpiece body with a convoluted acoustic horn, can be used with any suitable eartip, of any suitable design and made of any suitable material.

Ear Physiology and Fitting of Device in Ear

The physiology and features of a human ear will be briefly summarized so that the fitting of the present device into the ear of a user can be described in precise detail. With reference to FIG. 6, the external human ear 100 includes a broad structure 101 called the pinna. Pinna 101 includes a prominent exterior curved rim 103 called the helix, that originates in an upper base region 111 called the helix crus, and that extends therefrom in a counterclockwise direction along the radially outer edge of the pinna. Radially inward from the helix 103 is another curved prominence 107 called the antihelix, which extends from an upper base region 112 called the antihelix crura, in a generally counterclockwise direction so as to partially circumferentially surround a somewhat bowl-shaped depression 106 known as the concha. Concha 106 is at least partially divided by the helix crus 111 into a lower part 109 called the cavum concha, and an upper part 115 called the cimba concha. The inwardmost regions of concha 106 lead to the ear canal 104, which is a somewhat circular or oval (in cross-section) passage that leads to the eardrum and the inner ear.

The antihelix 107 exhibits a radially inward-facing rim 113 which, along at least some or most of its length, may protrude slightly radially inward so as to provide a lip or flange that slightly overhangs the radially outward edge of concha 106. The lowermost portion of the antihelix 107 (e.g., portion 116 as shown in FIG. 6) becomes the antitragus 108, which is a prominence that extends radially inward over the edge of the cavum concha (and which typically exhibits a more pronounced radially-inwardly-extending lip than does antihelix 107). Across the lower portion of the cavum concha from the antitragus is another radially-inward-extending prominence 105 called the tragus, which (in similar manner to the antitragus), typically exhibits a more pronounced lip than does the antihelix, and which may often slightly outwardly cover a portion of the ear canal 104.

Device 1 as disclosed herein is configured (sized and shaped) so that device 1 can be securely and comfortably retained in place in the ear of a user. While in some embodiments at least earpiece body 10 may be custom-made to fit a particular user's ear, in other embodiments the fit and retention of device 1 in a user's ear may be achieved without requiring device 1 to be custom-shaped to fit in the ear of that specific user. Thus in some embodiments device 1 (and earpiece body 10 and eartip 40 thereof) is not a custom-made device (e.g., a device of which any portion of any component is made according to a mold or 3-D image of the ear of a particular user). Moreover, in at least some embodiments, earpiece body 10 is at least semi-rigid or rigid and is not significantly compressible, or deformable in any manner, by the user in ordinary operation of device 1.

In at least some embodiments a device 1 may be configured so that it can fit in the right ear of a user and can also fit in the left ear of the user. In such embodiments it is not necessary to provide differently-configured (e.g., shaped) earpiece bodies 10 to be used in the right and left ears of a user; rather, a pair of identically shaped devices can be supplied. In other embodiments, earpiece bodies 10 may be supplied of somewhat different shape, for the right and left ear.

In some embodiments it may be useful to provide earpiece body with a relatively degree of bilateral symmetry in its overall shape. For example, earpiece body 10 may exhibit sufficient bilateral symmetry (i.e., when viewed along the inward-outward axis $IO_a$ of the earpiece body) to fit comfortably in a right ear or in a left ear, as desired. It is noted however that any desire for the overall shape of earpiece body 10 to have relatively high bilateral symmetry, does not require that the placement of various features (in particular, horn entrance 13 and protrusion 14) must necessarily exhibit bilateral symmetry. Nor does it preclude the presence of small, local asymmetries in the shape of earpiece body 10, as long as sufficient bilateral symmetry of the overall shape of earpiece body 10 is maintained.

The degree of overall bilateral symmetry of the shape of earpiece body 10 may be gauged by taking the projected area of earpiece body 10 on a plane that is substantially perpendicular to the inward-outward axis $IO_a$ of earpiece body 10, and identifying an axis of symmetry that runs at least generally along a long axis of the projected area and that divides the projected area into two (e.g. roughly equal) partial-areas. One of the partial-areas can then be rotated around the axis of symmetry onto the other partial-area (i.e., as if folding the projected area along the axis of symmetry to bring one partial-area over onto the other partial-area). The percentage of their areas that the two partial-areas share in common can be measured and represents the degree of bilateral symmetry that exists. By an earpiece body having an at least generally bilaterally symmetrical shape is meant that two partial-areas generated and measured in this manner share at least 70% of their area in common. (The bilateral symmetry of an exemplary earpiece body 10 may be most easily seen in the view of FIG. 4.) In various embodiments, earpiece body 10 may comprise a bilateral symmetry of at least about 80, 90, 95, or 98%.

In at least some embodiments, earpiece body 10 may exhibit an at least generally oval shape (when viewed along the long axis of eartip 40). The terminology of generally oval includes ovals, ellipses, rectangles with one or more rounded corners, teardrop shapes, and so on. In the specific embodiment illustrated in FIGS. 1-5, earpiece body 10 is of generally oval shape with end 31 (at which end eartip 40 is attached) being somewhat narrower than opposite end 32 (thus earpiece body 10 is somewhat teardrop-shaped, with a tapered end 31 and a blunt end 32, in this embodiment).

Shapes of these general types may allow one or more surfaces of earpiece body 10 to reside closely adjacent to (and in some embodiments to contact) a surface of an ear component that defines at least a portion of the radially outer perimeter of concha 106. Such ear components may include e.g. any or all of the tragus 105, the antitragus 108, and portions of the radially inward-facing rim 113 of the antihelix 107. Such arrangements can serve (e.g. in combination with the fitting of eartip 40 in ear canal 104) to retain device 1 securely and yet comfortably in the concha 106 of a human ear. This is illustrated in exemplary manner in FIG. 7, which shows an exemplary earpiece body 10 (with eartip 40 and ear canal 104 omitted from this view for ease of presentation) seated in the right ear of a human user.

The dimensions and shape of earpiece body 10 are thus configured so that earpiece body 10 can reside in the concha 106 (in specific embodiments, in the cavum concha 109) of a human ear. For example, inward surface 15 of earpiece body 10 may be shaped so that when device 1 is fitted in the ear, some or most of the area of inward surface 15 may be in contact with (skin) surfaces that define the inward limits of concha 106. (Although shown as relatively planar in the exemplary depictions of FIGS. 2 and 5, in some embodiments surface 15 may exhibit a curved (e.g., convex) shape.) And, as mentioned above, one or more contact surfaces of earpiece body 10 (e.g., surface 35 as shown in FIGS. 1-2) can be provided (whether spaced apart, or extending continuously) around at least a portion of the perimeter of earpiece body 10, which contact surface or surfaces are configured so that when device 1 is fitted in the ear of a user, at least one contact surface is in contact with a (skin) surface of an ear component that defines at least a portion of the radially outer perimeter of concha 106 (e.g., of cavum concha 109).

In some embodiments, earpiece body 10 can be sized and shaped so that at least one generally outward-facing or radially-outward-facing contact surface (e.g. surface 35) of earpiece body 10 is able to fit at least partially inwardly underneath (and in some embodiments, to contact) an inwardly-facing surface of a radially-inwardly-protruding edge (e.g., lip) of an ear component that defines a portion of the radially outer perimeter of the concha. Thus, in some embodiments, earpiece body 10 of earpiece body 10 may comprise various contact surfaces that are respectively configured to reside in radially-inward proximity, and/or in inward proximity, to a radially inward-facing surface (e.g., a radially-inward-protruding lip) of the tragus 105, of the antitragus 108, and/or of a portion 116 of the antihelix that is proximate the antitragus. (In this context, by a portion of the antihelix that is proximate the antitragus means a portion that is within about 25 mm of the radially-inwardmost-projecting part of the antitragus, measured in a clockwise direction around the antihelix.) One such configuration is shown in exemplary illustration in FIG. 7, in which a contact surface proximate of blunt end 32 of earpiece body 10 inwardly underlies, and may be in contact with, a portion of a lip of antitragus 108. Similarly, a contact surface of tapered end 31 of earpiece body 10 inwardly underlies, and may be in contact with, a portion of a lip of tragus 105. For many users, tapered end 31 of earpiece body 10 being "tucked under" the lip of tragus 105 in this manner, may be a primary mechanism in which the holding of earpiece body 10 in the concha is enabled or enhanced. However, it is emphasized that depending on the particular shape of the components of a particular user's ear, any individual contact surface (or portion thereof) or earpiece body 10, may or may not necessarily contact the (skin) surface of any particular ear component (that defines at least a portion of the radially outer perimeter of the concha of that user's ear).

Thus in broad summary, in some embodiments earpiece body 10 may be configured so that device 1 may be held in position in a human ear by way of at least one contact surface of earpiece body 10 of device 1 being adjacent to (e.g., in contact with) a skin surface that defines at least a portion of the radially outer perimeter of concha 106, in combination with the fitting of eartip 40 into ear canal 104. (Such arrangements may be distinguished from arrangements in which a device is substantially, or essentially, supported and held in place in the ear only by the fitting of an eartip of the device into the ear canal.) In further embodiments, earpiece body 10 may be configured so that device 1 may be held in position in a human ear at least in part by way of two or more contact surfaces of earpiece body 10 (e.g., at different locations along the radially outer perimeter of earpiece body 10) being adjacent to (e.g., in contact with) respective skin surfaces that define at least a portion of the radially outer perimeter of concha 106. In various embodiments, when device 1 is fitted into the ear of a user, two such areas of contact between contact surfaces of earpiece body 10 and surfaces of ear components defining portions of the radially outer perimeter of concha 106, may be spaced around the perimeter of earpiece body 10 with a circumferential separation of at least 120, 140, or 160 degrees (in either a clockwise or a counterclockwise direction). Such an arrangement is shown in exemplary embodiment FIG. 7, with two such areas of contact (with a portion of the tragus, and with a portion of the antitragus, respectively) having a circumferential separation judged to be in the range of about 130 degrees.

While in some embodiments the fitting of eartip 40 into ear canal 104 may augment the above effects in securely fitting device 1 into a human ear, the providing of at least one contact surface (and particularly, two or more such surfaces) around the perimeter of earpiece body 10 may allow for less aggressive fitting of eartip 40 into the ear canal (that is, eartip 40 may not need to be fitted as deep into the ear canal), thus providing increased comfort for the user while allowing device 1 to still be securely held in place. That is, in such embodiments eartip 40 may only need to be fitted into the ear canal to an extent sufficient to provide the aforementioned external occlusion rather than to serve as the primary mechanism for securing device 1 in the ear. Thus in some embodiments device 1 may be held in place in the ear partially, substantially or essentially completely by way of a compression fit of earpiece body 10 of device 1, between portions of components defining the radially outer perimeter of the concha, e.g. between any combination of a tragus, an antitragus, and/or a portion of an antihelix that is proximate the antitragus, of a user's ear.

In some embodiments, the inward-outward dimension of earpiece body 10 (i.e., the average distance between inward surface 15 and outward surface 16 may be kept to a minimum so that no portion of earpiece body 10 extends outward beyond an imaginary plane that coincides with the outwardmost limit of the antihelix. This may provide that device 1 may be comfortable to wear even when a user is sleeping (e.g., so that device 1 does not protrude so far outward that positioning the user's head and ear in contact with a pillow might cause device 1 to exert an uncomfortable force on the user's ear). In at least some embodiments, when device 1 is fitted into a user's ear, all parts of earpiece body 10 may be generally, substantially, or completely, located within the cavum concha. In particular, in some embodiments earpiece body 10 will not comprise any protrusion that, when device 1 is fitted into a user's ear, extends upward into the cimba concha (e.g., in the manner of an arcuate protrusion that follows, and/or rests radially inward of, the rim of the cimba concha).

In some embodiments, an offset angle may be present between long axis L of eartip 40 and earpiece body 10 (specifically, between long axis L of eartip 40 and the inward-outward axis $IO_a$ of earpiece body 10). Such an offset angle may provide enhanced comfort of device 1 when fitted into a user's ear. Thus, the exemplary design shown in FIGS. 1-5 provides an offset angle in the range of approximately 10-15 degrees. In various embodiments, such an offset angle may be at least about 6, 8, or 10 degrees. In further embodiments, such an offset angle may be at most about 18, 16, or 14 degrees. In many embodiments, the orientation of long axis L of eartip 40 may be dictated by the orientation of a mounting structure (e.g., protrusion 14) of earpiece body 10 to which eartip 40 is mounted. Thus, in many embodiments, such an offset angle may established e.g. by the angle at which protrusion 14 extends away from earpiece body 10 of earpiece body 10, as is the case in the exemplary embodiment best seen in FIG. 5.

The above discussions are to be interpreted in view of the fact there exists some variation in the shape of human ears. Thus, the descriptions provided herein of fitting device 1 into a human ear, e.g. a concha, will be understood as applying to adults with ear geometries and features that would be considered by an audiologist as being representative of the average adult population of humans. It is noted that device 1 (specifically, earpiece body 10 and/or eartip 40 thereof) may be provided in multiple sizes, with, for any device 1, the above descriptions being valid for at least the particular human population for which that size device 1 is configured. In specific embodiments, the fitting of device 1 into a concha as described herein may be evaluated with respect to the fitting of device 1 into an artificial ear (i.e., a molded plastic artificial pinna) suitable for use in the test methods outlined in ANSI S12.42 (Methods for the Measurement of Insertion Loss of Hearing Protection Devices in Continuous or Impulsive Noise Using Microphone-in-Real-Ear or Acoustic Test Fixture Procedures) as specified in 2010. A specific example of such artificial ears are those available under the trade designation KB0077 (left) and KB0078 (right) from G.R.A.S. Sound & Vibration A/S (Holte, Denmark) for use with the G.R.A.S. 45CB Acoustic Test Fixture. Thus, in specific embodiments, earpiece body 10 is configured to have at least one contact surface that is configured to contact a "skin" surface that defines at least a portion of the radially outer perimeter of a concha, of an artificial ear that meets the requirements for use with the ANSI S12.42 test method.

Although earpiece body 10 and eartip 40 have been described above in a configuration in which they are combined to form a hearing protection device 1, it is emphasized that in at least some embodiments earpiece body 10 may be supplied without an eartip attached thereto. That is, an earpiece body 10 may be supplied to a user who may then use it in combination with any suitable eartip. Moreover, in some embodiments at least one earpiece body and at least one eartip may be packaged together e.g. in the form of a kit. Such a kit may include instructions for use (noting that such instructions may be virtual instructions, e.g. in the form of a listed website that can be visited to read or upload a user guide or the like).

Although the discussions above have primarily concerned a passive hearing protection device, in other embodiments an earpiece body as disclosed herein may be used in an electronic hearing protection device. By this is meant a device that substantially prevents ambient airborne sound from directly entering the ear canal, and that includes electronic components that receive ambient airborne sound, convert the sound to electronic signals, process the electronic signals, convert the processed electronic signals into processed sound, and then emit the processed sound into the ear canal. It is emphasized however, that an earpiece body comprising a convoluted acoustic horn as disclosed herein, is configured for use in a hearing protection device (whether passive or electronic), which device is distinguished from both passive and electronic hearing-assistive devices (e.g., hearing aids, ear trumpets, and the like).

It is noted that in discussions herein, various devices, components and arrangements have been characterized as e.g. "substantially preventing" the passing of airborne sound waves. It will be understood that such terminology does not require that such a device, component or arrangement necessarily provide an absolute barrier to airborne sound. Rather, the only requirement signified by this terminology is that all such components and arrangements collectively provide sufficient barrier properties to airborne sound that device 1, comprising eartip 40 and earpiece body 10 as disclosed herein, is capable of functioning as disclosed herein.

LIST OF EXEMPLARY EMBODIMENTS

Embodiment 1 is an earpiece body that is configured to reside in the concha of a user's ear and that comprises a convoluted acoustic horn that is configured to receive airborne sound waves through a first, sound-receiving opening and to emit airborne sound waves through a second, sound-emitting opening, wherein the first, sound-receiving opening is larger in cross-sectional area than the second, sound-emitting opening by an incremental percentage of from about 150 to about 1600; wherein the second, sound-emitting opening is an offset opening; and wherein the first, sound-receiving opening and the second, sound-emitting opening are fluidly connected with each other so as to provide the convoluted acoustic horn; and, wherein the earpiece body is configured to accept an eartip that is attachable thereto, the eartip being configured to fit into the ear canal of the user's ear and the earpiece body and the eartip combining to provide a passive hearing protection device.

Embodiment 2 is the earpiece body of embodiment 1 wherein the first, sound-receiving opening is larger in area than the second, sound-emitting opening by an incremental percentage of from about 200 to about 1000. Embodiment 3 is the earpiece body of any of embodiments 1-2 wherein the first, sound-receiving opening is an at least generally outward-facing opening. Embodiment 4 is the earpiece body of any of embodiments 1-3 wherein the convoluted acoustic horn comprises a length, from the first, sound-receiving opening to the second, sound-emitting opening, of from about 3 cm to about 5 cm. Embodiment 5 is the earpiece body of any of embodiments 1-4 wherein the convoluted acoustic horn is in the form of an offset spiral in which no portion of the second, sound-emitting opening of the convoluted acoustic horn is in overlapping relation with any portion of the first, sound-receiving opening of the convoluted acoustic horn.

Embodiment 6 is the earpiece body of any of embodiments 1-5 wherein the convoluted acoustic horn exhibits an overall taper in the range of from about 50 to about 400 incremental percentage change, per centimeter of horn length. Embodiment 7 is the earpiece body of any of embodiments 1-6 wherein the convoluted acoustic horn exhibits a taper that is at least substantially constant over at least about 80% of the length of the convoluted acoustic horn. Embodiment 8 is the earpiece body of any of embodiments 1-7 wherein the cross-sectional area of the first, sound-receiving opening of the convoluted acoustic horn is in the range of about 30-45 square mm. Embodiment 9 is the earpiece body of any of embodiments 1-8 wherein the convoluted acoustic horn exhibits one or two underpass features.

Embodiment 10 is the earpiece body of any of embodiments 1-9 wherein the earpiece body exhibits an at least generally bilaterally symmetrical shape when viewed along an inward-outward axis of the earpiece body. Embodiment 11 is the earpiece body of any of embodiments 1-10 wherein the earpiece body exhibits a long axis that is oriented at least substantially orthogonal to an inward-outward axis of the earpiece body. Embodiment 12 is the earpiece body of any of embodiments 1-11 comprising a mechanical switch located on an outward face of the earpiece body, which mechanical switch is operatively connected to a valve so that the mechanical switch can be used to at least partially close the valve so as to at least partially block the airborne transmission of sound through the convolute acoustic horn. Embodiment 13 is the earpiece body of embodiment 12 wherein the valve is located proximate the second, sound-emitting opening of the acoustic horn.

Embodiment 14 is a passive hearing protection device configured to fit in the ear of a human user, comprising: an earpiece body that is configured to reside in the concha of a user's ear and that comprises a convoluted acoustic horn that is configured to receive airborne sound waves through a first, sound-receiving opening and to emit airborne sound waves through a second, sound-emitting opening, wherein the first, sound-receiving opening is larger in cross-sectional area than the second, sound-emitting opening by an incremental percentage of from about 150 to about 1400; wherein the second, sound-emitting opening is an offset opening; and wherein the first, sound-receiving opening and the second, sound-emitting opening are fluidly connected with each other so as to provide the convoluted acoustic horn; and, an eartip configured to fit into the ear canal of the user's ear, the eartip being attached to the earpiece body and comprising an airborne-sound-transmissive through-passage with a primary, sound-receiving opening that is configured to receive airborne sound that has passed through the convoluted horn of the earpiece body and with a secondary, sound-emitting opening that faces toward the inner ear of the user.

Embodiment 15 is the device of embodiment 14 wherein the device comprises a sound-level-dependent sound attenuating physical feature that is located between the second, sound-emitting opening of the acoustic horn and the primary, sound-receiving opening of the eartip so that any airborne sound that is emitted from the second, sound-emitting opening of the acoustic horn must encounter the sound-level-dependent sound attenuating physical feature before reaching the primary, sound-receiving opening of the eartip. Embodiment 16 is the device of embodiment 15 wherein the sound-level-dependent sound attenuating physical feature is an acoustic filter that is fitted into a chamber defined at least partially by surfaces molded into the interior of a protruding post of the earpiece body and through which sound that is emitted from the second, sound-emitting opening of the acoustic horn must pass to reach the primary, sound-receiving opening of the eartip.

Embodiment 17 is the device of any of embodiments 14-16 wherein the earpiece body comprises at least one contact surface that is configured so that when the device is fitted in the ear of a user, the at least one contact surface contacts a skin surface of an ear component that defines at least a portion of a radially outer perimeter of the concha of the user's ear. Embodiment 18 is the device of embodiment 17 wherein the at least one contact surface of the earpiece body is configured so that when the device is fitted in the ear of a user, the at least one contact surface contacts at least one of a skin surface of a tragus, an antitragus, and a portion of an antihelix that is proximate the antitragus, of the user's ear. Embodiment 19 is the device of embodiment 18 wherein the earpiece body is configured so that when the device is fitted into the user's ear, the device is held in the ear at least in part by a compression fit of the earpiece body of the device, with at least any two of a tragus, an antitragus, and a portion of an antihelix that is proximate the antitragus, of the user's ear.

Embodiment 20 is the device of any of embodiments 14-19 wherein the earpiece body is configured so that when the device is fitted into the user's ear, the earpiece body resides at least substantially in the cavum concha of a user's ear. Embodiment 21 is the device of embodiment 20 wherein the earpiece body is configured so that when the device is fitted into the user's ear, at least substantially no portion of the earpiece body extends into the cimba concha of the user's ear. Embodiment 22 is the device of any of embodiments 14-21 wherein the earpiece body is configured so that when the device is fitted into the user's ear, at least substantially no portion of the earpiece body extends outward, along an inward-outward axis of the earpiece body, of the concha of the user's ear. Embodiment 23 is the device of embodiment 14 comprising the earpiece body of any of embodiments 1-13.

Embodiment 24 is a kit comprising: at least one earpiece body that is configured to reside in the concha of a user's ear and that comprises a convoluted acoustic horn that is configured to receive airborne sound waves through a first, sound-receiving opening and to emit airborne sound waves through a second, sound-emitting opening, wherein the first, sound-receiving opening is larger in cross-sectional area than the second, sound-emitting opening by an incremental percentage of from about 150 to about 1400; wherein the second, sound-emitting opening is an offset opening; and wherein the first, sound-receiving opening and the second, sound-emitting opening are fluidly connected with each other so as to provide the convoluted acoustic horn; and, at least one eartip configured to fit into the ear canal of the user's ear, the eartip being further configured to be attachable to the earpiece body. Embodiment 25 is the kit of embodiment 24 wherein the at least one earpiece body is the earpiece body of any of embodiments 1-13.

EXAMPLE

Figure 8:
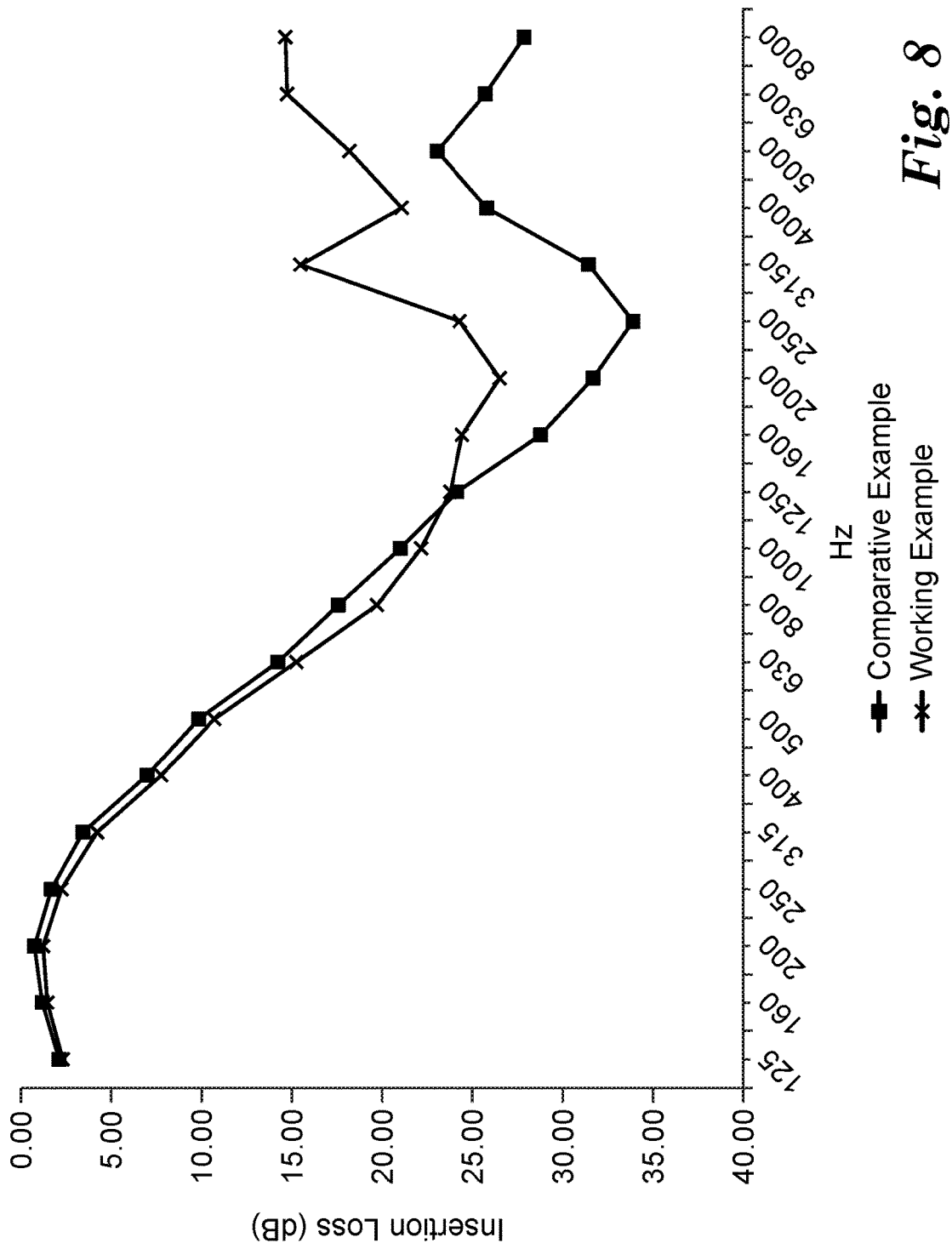
FIG. 8 presents Insertion Loss data for a Working Example hearing protection device, in comparison to a conventional hearing protection device.

A Working Example earpiece body was made by rapid prototyping methods (stereolithography), of a design generally similar to that shown in FIGS. 1-5. In this prototype, the earpiece body was an otherwise solid structure (made of plastic) comprising a convoluted, helical acoustic horn of similar layout to that seen most easily in FIG. 4. The horn had an outward-facing, circular, unobstructed entrance of 37 mm$^2$ in area, a generally inward-facing exit of approximately 2.7 mm$^2$ in area, and a path length of approximately 4 cm. The earpiece body comprised a protrusion of similar design to that seen most easily in FIGS. 2 and 5, which protrusion included a chamber into which was placed a level-dependent acoustic filter of the type used in the hearing-protection product available from 3M Company under the trade designation COMBAT ARMS EARPLUGS. An eartip of generally similar type depicted in FIGS. 1-2 was press-fitted onto the protrusion of the earpiece body to form a Working Example passive hearing protection device. The hearing protection device was positioned in the ear of a KEMAR G.R.A.S. 45CB manikin. The insertion loss (measured relative to the G.R.A.S. 45CB manikin in the absence of the prototype hearing protection device) was measured by conventional methods (using pink noise) and is presented in FIG. 8.

For comparison, the insertion loss was similarly measured for a conventional passive hearing protection device (that did not include any kind of acoustic horn, but that did include the same acoustic filter that was used in the Working Example and that also used the same eartip that was used in the Working Example). It is evident that the Working Example exhibited significantly less Insertion Loss than the conventional hearing protection device, particularly in a frequency range above approximately 2000 Hz.

The foregoing Example has been provided for clarity of understanding only, and no unnecessary limitations are to be understood therefrom. The tests and test results described in the Examples are intended to be illustrative rather than predictive, and variations in the testing procedure can be expected to yield different results. All quantitative values in the Examples are understood to be approximate in view of the commonly known tolerances involved in the procedures used. It will be apparent to those skilled in the art that the specific exemplary elements, structures, features, details, configurations, etc., that are disclosed herein can be modified and/or combined in numerous embodiments. (In particular, any of the elements that are positively recited in this specification as alternatives, may be explicitly included in the claims or excluded from the claims, in any combination as desired.) All such variations and combinations are contemplated by the inventor as being within the bounds of the conceived invention not merely those representative designs that were chosen to serve as exemplary illustrations. Thus, the scope of the present invention should not be limited to the specific illustrative structures described herein, but rather extends at least to the structures described by the language of the claims, and the equivalents of those structures. To the extent that there is a conflict or discrepancy between this specification as written and the disclosure in any document incorporated by reference herein, this specification as written will control.

What is claimed is:

1. An earpiece body that is configured to reside in the concha of a user's ear and that comprises a convoluted acoustic horn that is configured to receive airborne sound waves through a first, sound-receiving opening and to emit airborne sound waves through a second, sound-emitting opening, wherein the first, sound-receiving opening is larger in cross-sectional area than the second, sound-emitting opening by an incremental percentage of from about 150 to about 1600; wherein the second, sound-emitting opening is an offset opening; and wherein the first, sound-receiving opening and the second, sound-emitting opening are fluidly connected with each other so as to provide the convoluted acoustic horn;

and, wherein the earpiece body is configured to accept an eartip that is attachable thereto, the eartip being configured to fit into the ear canal of the user's ear and the earpiece body and the eartip combining to provide a passive hearing protection device.

2. The earpiece body of claim 1 wherein the first, sound-receiving opening is larger in area than the second, sound-emitting opening by an incremental percentage of from about 200 to about 1000.

3. The earpiece body of claim 1 wherein the first, sound-receiving opening is an at least generally outward-facing opening.

4. The earpiece body of claim 1 wherein the convoluted acoustic horn comprises a length, from the first, sound-receiving opening to the second, sound-emitting opening, of from about 3 cm to about 5 cm.

5. The earpiece body of claim 1 wherein the convoluted acoustic horn is in the form of an offset spiral in which no portion of the second, sound-emitting opening of the convoluted acoustic horn is in overlapping relation with any portion of the first, sound-receiving opening of the convoluted acoustic horn.

6. The earpiece body of claim 1 wherein the convoluted acoustic horn exhibits an overall taper in the range of from about 50 to about 400 incremental percentage change, per centimeter of horn length.

7. The earpiece body of claim 1 wherein the convoluted acoustic horn exhibits a taper that is at least substantially constant over at least about 80% of the length of the horn.

8. The earpiece body of claim 1 wherein the cross-sectional area of the first, sound-receiving opening of the convoluted acoustic horn is in the range of about 30-45 square mm.

9. The earpiece body of claim 1 wherein the convoluted acoustic horn exhibits one or two underpass features.

10. The earpiece body of claim 1 wherein the earpiece body exhibits an at least generally bilaterally symmetrical shape when viewed along an inward-outward axis of the earpiece body.

11. The earpiece body of claim 1 wherein the earpiece body exhibits a long axis that is oriented at least substantially orthogonal to an inward-outward axis of the earpiece body.

12. The earpiece body of claim 1 comprising a mechanical switch located on an outward face of the earpiece body, which mechanical switch is operatively connected to a valve so that the mechanical switch is operative to at least partially close the valve so as to at least partially block the airborne transmission of sound through the convolute acoustic horn.

13. The earpiece body of claim 12 wherein the valve is located proximate the second, sound-emitting opening of the acoustic horn.

14. A passive hearing protection device configured to fit in the ear of a human user, comprising:

an earpiece body that is configured to reside in the concha of a user's ear and that comprises a convoluted acoustic horn that is configured to receive airborne sound waves through a first, sound-receiving opening and to emit airborne sound waves through a second, sound-emitting opening, wherein the first, sound-receiving opening is larger in cross-sectional area than the second, sound-emitting opening by an incremental percentage of from about 150 to about 1400; wherein the second, sound-emitting opening is an offset opening; and wherein the first, sound-receiving opening and the second, sound-emitting opening are fluidly connected with each other so as to provide the convoluted acoustic horn;

and, an eartip configured to fit into the ear canal of the user's ear, the eartip being attached to the earpiece body and comprising an airborne-sound-transmissive through-passage with a primary, sound-receiving opening that is configured to receive airborne sound that has passed through the convoluted horn of the earpiece body and with a secondary, sound-emitting opening that faces toward the inner ear of the user.

15. The device of claim 14 wherein the device comprises a sound-level-dependent sound attenuating physical feature that is located between the second, sound-emitting opening of the acoustic horn and the primary, sound-receiving opening of the eartip so that any airborne sound that is emitted from the second, sound-emitting opening of the acoustic horn must encounter the sound-level-dependent sound attenuating physical feature before reaching the primary, sound-receiving opening of the eartip.

16. The device of claim 15 wherein the sound-level-dependent sound attenuating physical feature is an acoustic filter that is fitted into a chamber defined at least partially by surfaces molded into the interior of a protruding post of the earpiece body and through which sound that is emitted from the second, sound-emitting opening of the acoustic horn must pass to reach the primary, sound-receiving opening of the eartip.

17. The device of claim 14 wherein the earpiece body comprises at least one contact surface that is configured so that when the device is fitted in the ear of a user, the at least one contact surface contacts a skin surface of an ear component that defines at least a portion of a radially outer perimeter of the concha of the user's ear.

18. The device of claim 17 wherein the at least one contact surface of the earpiece body is configured so that when the device is fitted in the ear of a user, the at least one contact surface contacts at least one of a skin surface of a tragus, an antitragus, and a portion of an antihelix that is proximate the antitragus, of the user's ear.

19. The device of claim 18 wherein the earpiece body is configured so that when the device is fitted into the user's ear, the device is held in the ear at least in part by a compression fit of the earpiece body of the device, with at least any two of a tragus, an antitragus, and a portion of an antihelix that is proximate the antitragus, of the user's ear.

20. The device of claim 14 wherein the earpiece body is configured so that when the device is fitted into the user's ear, the earpiece body resides at least substantially in the cavum concha.

21. The device of claim 20 wherein the earpiece body is configured so that when the device is fitted into the user's ear, at least substantially no portion of the earpiece body extends into the cimba concha of the user's ear.

22. The device of claim 14 wherein the earpiece body is configured so that when the device is fitted into the user's ear, at least substantially no portion of the earpiece body extends outward, along an inward-outward axis of the earpiece body, of the concha of the user's ear.

23. A kit comprising:

at least one earpiece body that is configured to reside in the concha of a user's ear and that comprises a convoluted acoustic horn that is configured to receive airborne sound waves through a first, sound-receiving opening and to emit airborne sound waves through a second, sound-emitting opening,
wherein the first, sound-receiving opening is larger in cross-sectional area than the second, sound-emitting opening by an incremental percentage of from about 150 to about 1400; wherein the second, sound-emitting opening is an offset opening; and wherein the first, sound-receiving opening and the second, sound-emitting opening are fluidly connected with each other so as to provide the convoluted acoustic horn;

and, at least one eartip configured to fit into the ear canal of the user's ear, the eartip being further configured to be attachable to the earpiece body to provide a passive hearing protection device.

* * * * *